US010012600B2

(12) United States Patent
Kang et al.

(10) Patent No.: US 10,012,600 B2
(45) Date of Patent: Jul. 3, 2018

(54) X-RAY APPARATUS AND METHOD OF CONTROLLING THE SAME

(71) Applicant: SAMSUNG ELECTRONICS CO., LTD., Suwon-si (KR)

(72) Inventors: Dong-Goo Kang, Hwaesong-si (KR); Young Hun Sung, Hwaseong-si (KR); Kye Young Jeong, Yongin-si (KR); Jiyoung Choi, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 183 days.

(21) Appl. No.: 14/829,769

(22) Filed: Aug. 19, 2015

(65) Prior Publication Data
US 2016/0091438 A1 Mar. 31, 2016

(30) Foreign Application Priority Data

Sep. 26, 2014 (KR) ........................ 10-2014-0129151

(51) Int. Cl.
| | |
|---|---|
| *G01N 23/04* | (2018.01) |
| *G06T 7/00* | (2017.01) |
| *A61B 6/00* | (2006.01) |
| *G06T 7/13* | (2017.01) |

(52) U.S. Cl.
CPC ............ *G01N 23/04* (2013.01); *A61B 6/405* (2013.01); *A61B 6/463* (2013.01); *A61B 6/482* (2013.01); *A61B 6/50* (2013.01); *A61B 6/502* (2013.01); *G06T 7/13* (2017.01); *G06T 2207/10116* (2013.01); *G06T 2207/20192* (2013.01)

(58) Field of Classification Search
CPC ......... A61B 6/482; A61B 6/405; A61B 6/463; G06T 2207/1106; G06T 2207/20192; G06T 7/13; G01N 23/04
See application file for complete search history.

(56) References Cited

U.S. PATENT DOCUMENTS

| | | | | |
|---|---|---|---|---|
| 7,583,779 B2 * | 9/2009 | Tkaczyk | ............... | A61B 6/032 378/4 |
| 7,599,465 B2 * | 10/2009 | Walter | .................. | A61B 6/032 378/4 |
| 7,920,735 B2 * | 4/2011 | Krauss | .................. | A61B 6/482 378/21 |
| 8,189,896 B2 * | 5/2012 | Kawamura | ............ | G06T 7/337 382/132 |
| 8,213,701 B2 * | 7/2012 | Tsuchiya | ................ | G06T 5/002 382/132 |
| 8,761,485 B2 * | 6/2014 | Jang | ...................... | G06T 7/0016 378/4 |
| 9,204,847 B2 * | 12/2015 | Flohr | .................. | A61B 6/4014 |

(Continued)

*Primary Examiner* — David J Makiya
*Assistant Examiner* — Soorena Kefayati
(74) *Attorney, Agent, or Firm* — Sughrue Mion, PLLC

(57) ABSTRACT

An X-ray apparatus includes an X-ray source configured to radiate X-rays onto an object, an X-ray detector configured to detect X-rays having penetrated through the object among the radiated X-rays and obtain pieces of raw data of different energy bands based on the detected X-rays, a raw image obtainer configured to obtain raw images in which different materials constituting the object are enhanced using the pieces of raw data, and an image processor configured to process the raw images and generate an X-ray image of the object based on the processed raw images.

22 Claims, 13 Drawing Sheets

(56) References Cited

U.S. PATENT DOCUMENTS

| | | | |
|---|---|---|---|
| 9,532,750 B2* | 1/2017 | Dzyubak | A61B 6/032 |
| 9,532,759 B2* | 1/2017 | Taguchi | A61B 6/032 |
| 2007/0092127 A1* | 4/2007 | Grasruck | G06T 5/50 |
| | | | 382/132 |
| 2008/0253508 A1* | 10/2008 | Krauss | A61B 6/032 |
| | | | 378/19 |
| 2010/0067772 A1* | 3/2010 | Kitamura | A61B 6/482 |
| | | | 382/132 |
| 2011/0164797 A1* | 7/2011 | Jang | G06T 7/0016 |
| | | | 382/130 |
| 2011/0255654 A1* | 10/2011 | Kim | A61B 6/482 |
| | | | 378/5 |
| 2012/0063662 A1* | 3/2012 | Kwon | G06T 5/003 |
| | | | 382/132 |
| 2013/0142412 A1* | 6/2013 | Oh | A61B 6/4241 |
| | | | 382/132 |
| 2016/0267651 A1* | 9/2016 | Maack | A61B 6/482 |

* cited by examiner

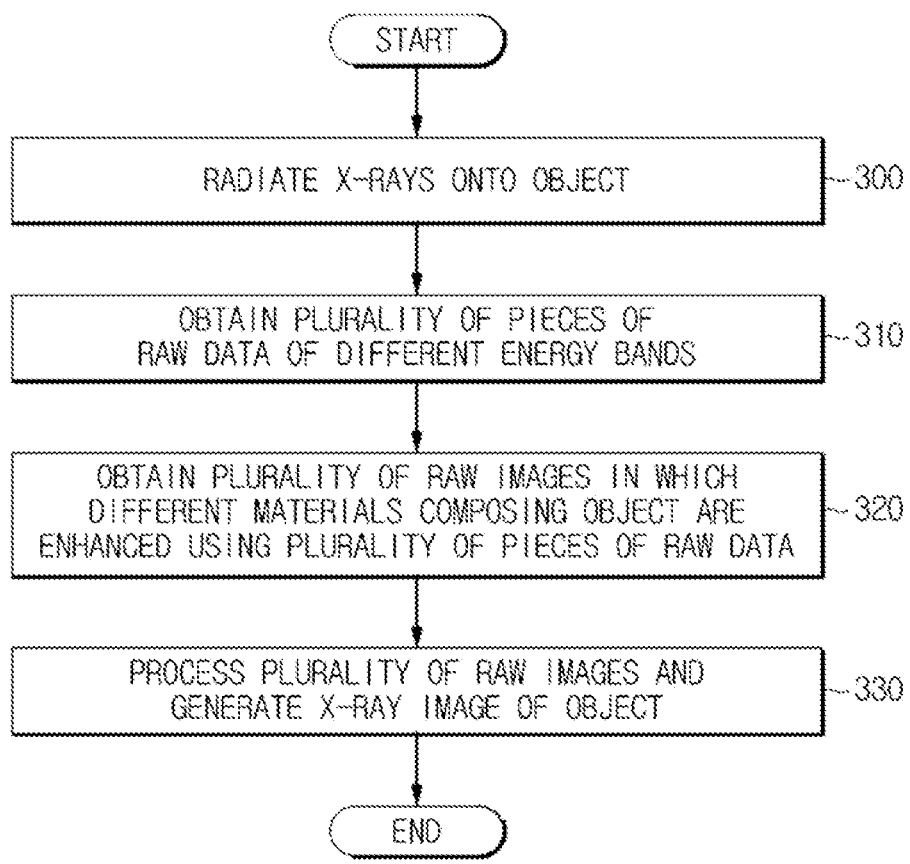

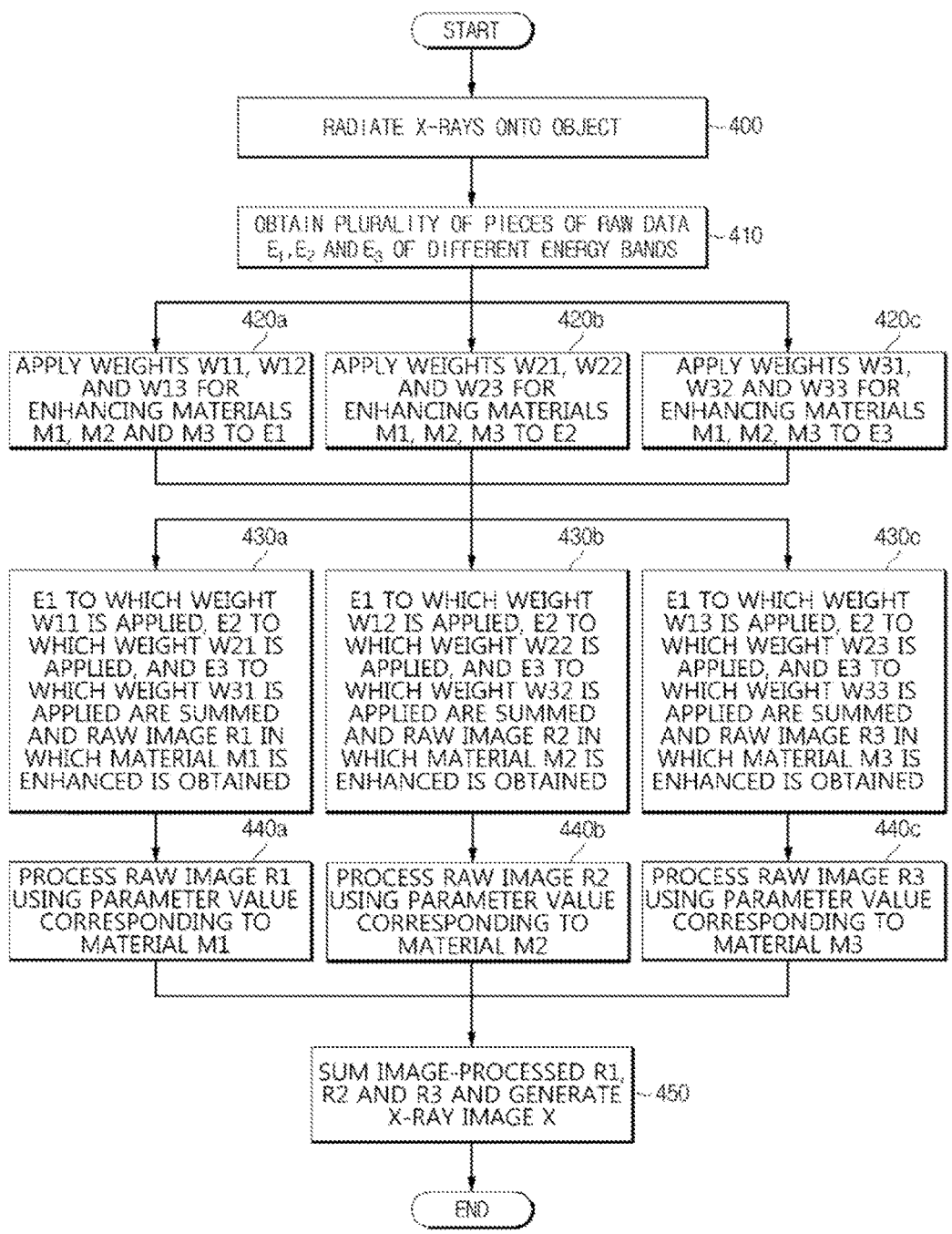

X-RAY APPARATUS AND METHOD OF CONTROLLING THE SAME

CROSS-REFERENCE TO RELATED APPLICATION

This application claims the benefit of Korean Patent Application No. 10-2014-129151, filed on Sep. 26, 2014 in the Korean Intellectual Property Office, the disclosure of which is incorporated herein by reference in its entirety.

BACKGROUND

1. Field

Exemplary embodiments consistent with the present disclosure relate to an X-ray apparatus for generating an X-ray image by penetrating X-rays through an object and a method of controlling the same.

2. Description of the Related Art

An X-ray imaging apparatus is an apparatus capable of obtaining an internal image of an object by radiating X-rays onto the object and using the X-rays having penetrated through the object. Since permeability of X-rays differs depending on properties of a material constituting the object, it is possible to image an internal structure of the object by detecting an intensity or a strength of X-rays having penetrated through the object.

Specifically, when an X-ray generating unit generates X-rays and radiates the X-rays onto the object, an X-ray detecting unit detects X-rays having penetrated through the object and converts the detected X-rays into an electrical signal. Since converting the X-rays into the electrical signal is performed on each pixel, it is possible to obtain a single X-ray image by combining electrical signals corresponding to pixels.

Recently, a variety of research on a material image that is obtained by separating materials constituting the object from the X-ray image obtained in this manner is being conducted. The material image may be used to distinguish a calcified nodule and a non-calcified nodule or distinguish a part in which fine tissues overlap with each other from a nodule.

SUMMARY

According to exemplary embodiments of an X-ray apparatus and a method of controlling the same, there are provided an X-ray apparatus for obtaining an X-ray image having improved image quality for each material by applying a material-adaptive weight to X-ray data and a method of controlling the same.

According to an aspect of an exemplary embodiment, there is provided an X-ray apparatus, including an X-ray source configured to radiate X-rays onto an object; an X-ray detector configured to detect X-rays having penetrated through the object among the detected X-rays and obtain pieces of raw data of different energy bands based on the detected X-rays; a raw image obtainer configured to obtain raw images in which different materials constituting the object are enhanced using the pieces of raw data; and an image processor configured to process the raw images and generate an X-ray image of the object based on the processed raw images.

According to another aspect of an exemplary embodiment, there is provided a method of controlling an X-ray apparatus, including: radiating X-rays onto an object; detecting X-rays having penetrated through the object among the radiated X-rays and obtaining pieces of raw data of different energy bands based on the detected X-rays; obtaining raw images in which different materials constituting the object are enhanced using the pieces of raw data; and processing the raw images and generating an X-ray image of the object based on the processed raw images.

BRIEF DESCRIPTION OF THE DRAWINGS

These and/or other aspects of the exemplary embodiments will become apparent and more readily appreciated from the following description of the exemplary embodiments, taken in conjunction with the accompanying drawings of which:

FIG. 11 is a flowchart schematically illustrating a method of generating an X-ray image according to an exemplary embodiment; and FIG. 12 is a detailed flowchart illustrating a method of generating an X-ray image according to an exemplary embodiment.

DETAILED DESCRIPTION

Hereinafter, exemplary embodiments of an X-ray apparatus and a method of controlling the same according to an aspect of exemplary embodiments will be described in detail with reference to the accompanying drawings.

The X-ray apparatus may have different structures or imaging methods according to an imaging area, a type of an X-ray image, or an imaging purpose. Specifically, the X-ray apparatus includes a general X-ray apparatus for imaging a chest, an arm, a leg, and the like, an X-ray apparatus using mammography that is a breast imaging technique, an X-ray apparatus using fluoroscopy, an X-ray apparatus using angiography or cardiovascular angiography, an X-ray apparatus using computed tomography, and the like. An X-ray apparatus to be described may be any of the above X-ray apparatuses or a combination of two or more types of X-ray apparatuses.

Figure 1A:
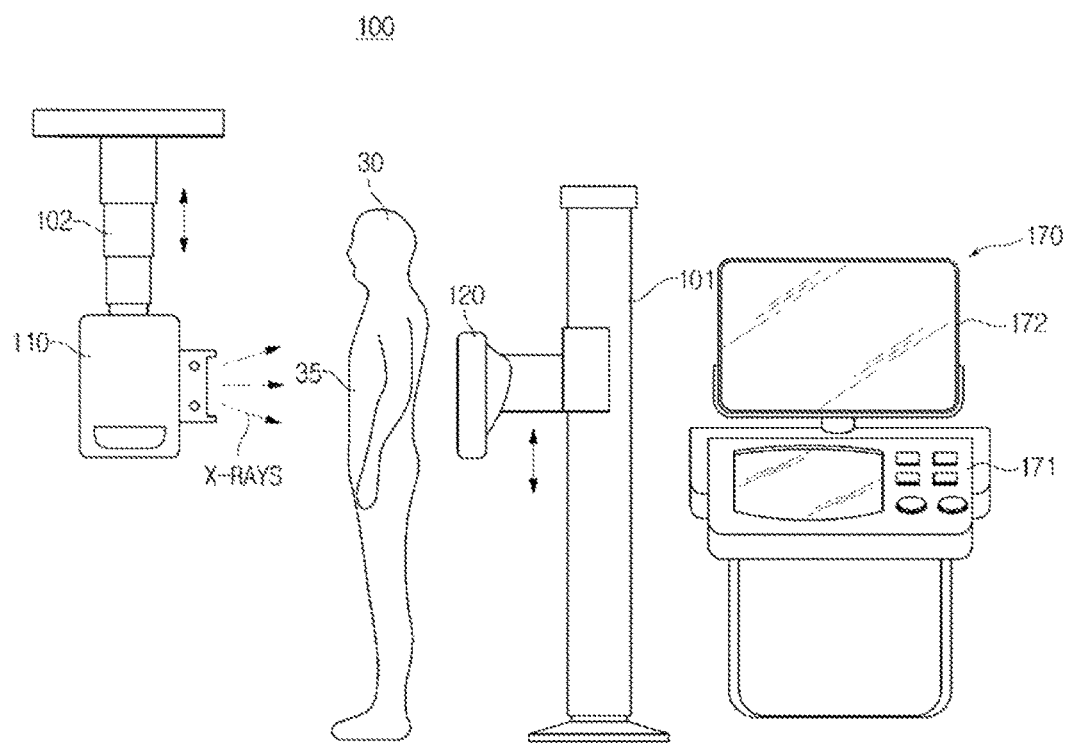
FIGS. 1A and 1B are diagrams illustrating exemplary appearances of several exemplary embodiments of an X-ray apparatus.
Figure 1B:
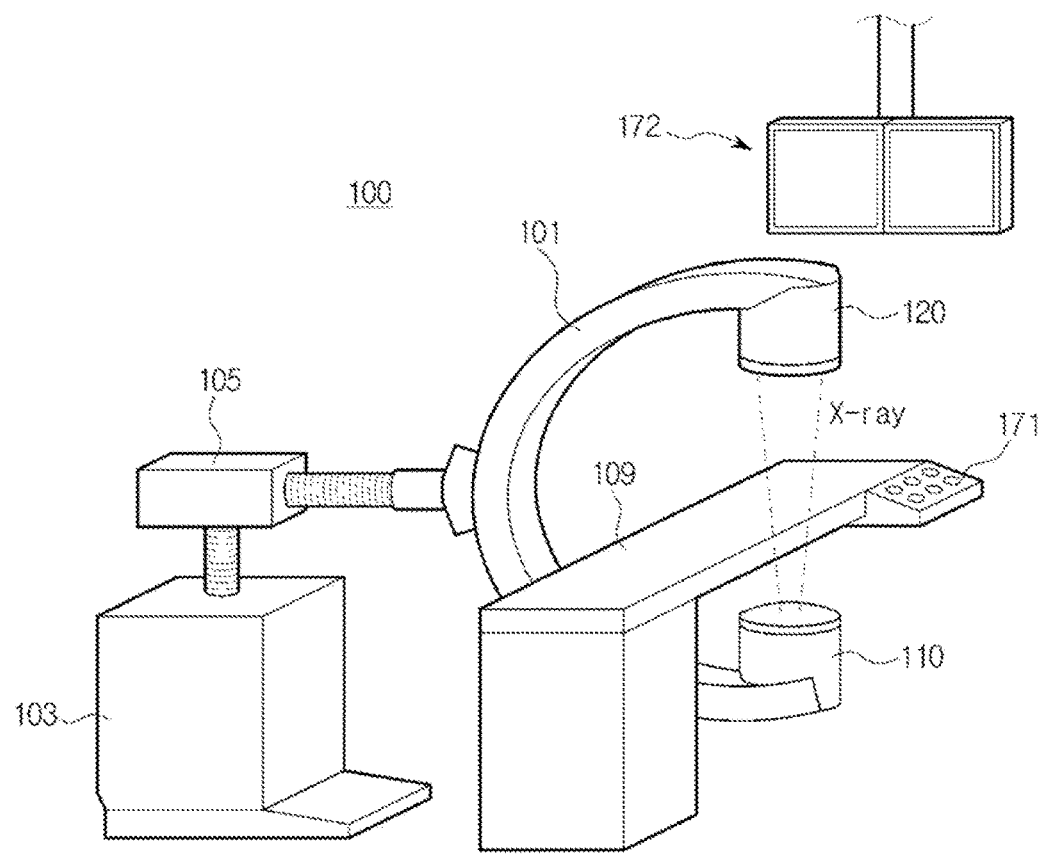

FIGS. 1A and 1B are diagrams illustrating exemplary appearances of several exemplary embodiments of an X-ray apparatus.

As illustrated in FIG. 1A, an X-ray apparatus may include an X-ray source 110, an X-ray detector 120, and a host device 170.

The X-ray generating unit 110 may generate X-rays and radiate the generated X-rays onto a subject 30 in order to obtain an X-ray image of an object 35.

Here, the subject 30 may be a body of a human or an animal, but the exemplary embodiments are not limited thereto. The subject 30 may be any subject whose internal structure can be imaged by an X-ray apparatus 100.

In addition, the object 35 may refer to an area to be diagnosed inside the subject 30 using the X-ray apparatus 100, that is, an X-ray imaging area. Therefore, as illustrated in FIG. 1, when the subject 30 lies on a table, the object 35 may be a head, a chest, an arm, a leg, or the like.

The X-ray source 110 may be mounted to be movable in a lengthwise direction of the table from a ceiling. When the X-ray source 110 moves in the lengthwise direction of the table, a position of the X-ray source 110 may correspond to a position of the object 35.

The X-ray detector 120 is provided to face the X-ray source 110 by interposing the object 35 therebetween, and may detect X-rays that have been radiated from the X-ray source 110 and penetrated through the object 35. In addition, the X-ray detector 120 may convert the detected X-rays into X-ray data that is an electrical signal.

The X-ray detector 120 may be mounted inside the table to be movable in the lengthwise direction of the table. Similar to the X-ray source 110, a position of the X-ray detector 120 may be moved to correspond to a position of the object 35 in the lengthwise direction of the table.

Also, if the subject 30 lies on the table, the X-ray source 110 may be mounted to be movable in the lengthwise direction of the table from the ceiling, and the X-ray detector 120 may be mounted inside the table to be movable in the lengthwise direction of the table.

The host device 170 may provide a user interface by including an input unit 171 configured to receive a command from a user and a display 172 configured to display an X-ray image. According to an exemplary embodiment, the user may be a person who performs diagnosis of the object 35 using the X-ray apparatus 100 and may include a medical staff member such as a doctor, a radiologist, or a nurse, but the user is not limited thereto and includes anyone who uses the X-ray apparatus 100.

The input unit 171 may include at least one of a switch, a keyboard, a trackball, and a touch screen, but the exemplary embodiments are not limited thereto.

The display 172 may include a cathode ray tube (CRT), a liquid crystal display (LCD), a light emitting diode (LED), or the like, but the exemplary embodiments are not limited thereto.

As illustrated in FIG. 1B, the X-ray apparatus 100 may have a C-arm structure. The X-ray source 110 and the X-ray detector 120 may be mounted at each end of a C-arm 101 having a C shape. The C-arm 101 is connected to a main body 103 through a connecting shaft 105 and is rotatable in an orbital direction.

A patient table 109 is provided between the X-ray source 110 and the X-ray detector 120. When the object is positioned on the patient table 109, the X-ray source 110 radiates X-rays onto the object, the X-ray detector 120 detects the radiated X-rays, and thereby the X-ray image of the object is obtained.

The X-ray apparatus 100 may perform X-ray imaging according to various imaging modes. When the X-ray apparatus provides a live video of the object, the user may perform a procedure or diagnosis while watching the display 172 that has a plurality of screens and can display several images to be used for the procedure or diagnosis.

The user may input information through the input unit 171 provided in the X-ray apparatus 100. For example, the input unit may receive a control command such as a power control command of the X-ray apparatus, an X-ray radiation control command of the X-ray source 110, an X-ray detection control command of the X-ray detector, and a mode control command of an X-ray image displayed by the display 172, or object information used for X-ray imaging.

Figure 2:
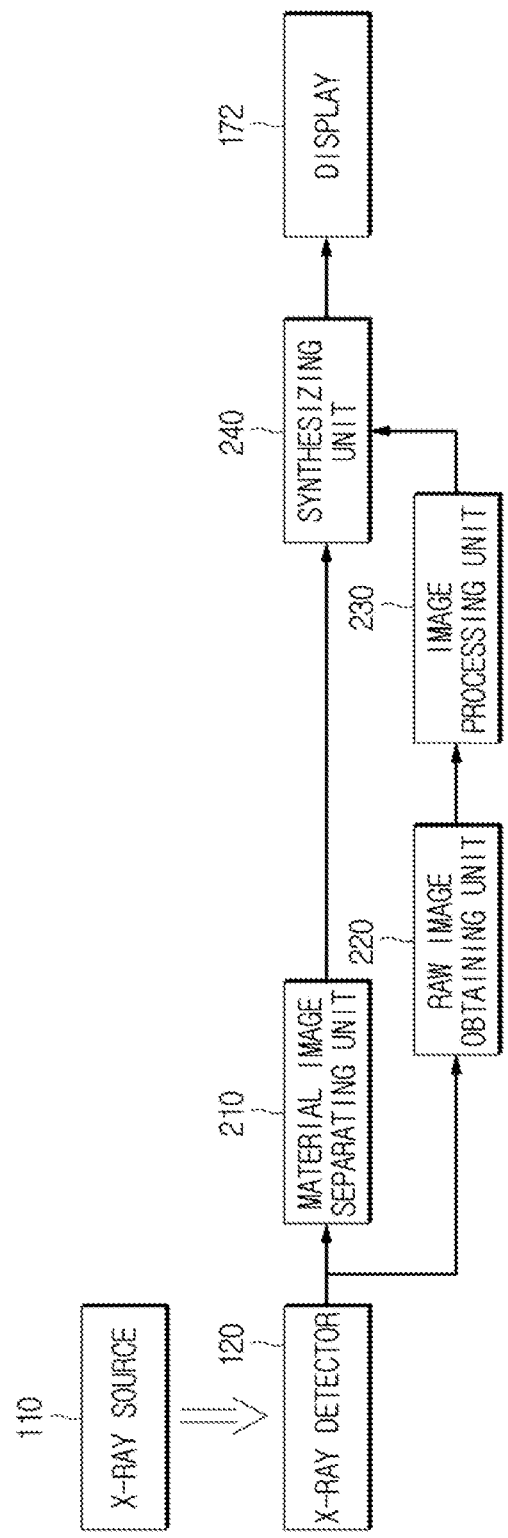
FIG. 2 is a control block diagram of an X-ray apparatus according to an exemplary embodiment.

FIG. 2 is a control block diagram of an X-ray apparatus according to an exemplary embodiment.

According to an exemplary embodiment of the X-ray apparatus, the X-ray apparatus may include the X-ray source 110 configured to generate X-rays and radiate the X-rays onto the object 35; the X-ray detector 120 configured to detect X-rays having penetrated through the object 35 and obtain raw data; a material image separating unit 210 (e.g., material image separator) configured to generate at least one material image separated from the object using raw data; a raw image obtaining unit 220 (e.g., raw image obtainer) configured to obtain a plurality of raw images in which different materials constituting the object are enhanced using raw data; an image processing unit 230 (e.g., image processor) configured to process a plurality of raw images and generate an X-ray image of the object; a synthesizing unit 240 (e.g., synthesizer) configured to synthesize the X-ray image of the object and at least one material image; and the display 172 configured to display the synthesized image.

The X-ray source 110 generates X-rays and radiates the X-rays onto the object 35. The X-ray source 110 receives power from a power supply unit and generates X-rays. Energy of X-rays may be controlled by a tube voltage. An intensity or a dose of X-rays may be controlled by a tube current and an X-ray exposure time.

The X-ray source 110 may radiate monochromatic X-rays or polychromatic X-rays. Hereinafter, it is assumed that the X-ray source 110 radiates polychromatic X-rays having a predetermined energy band, that is, multi-energy X-rays, and the energy band of radiated X-rays is defined by an upper limit and a lower limit.

The X-ray source 110 includes an X-ray tube 111 configured to generate X-rays.

Figure 3:
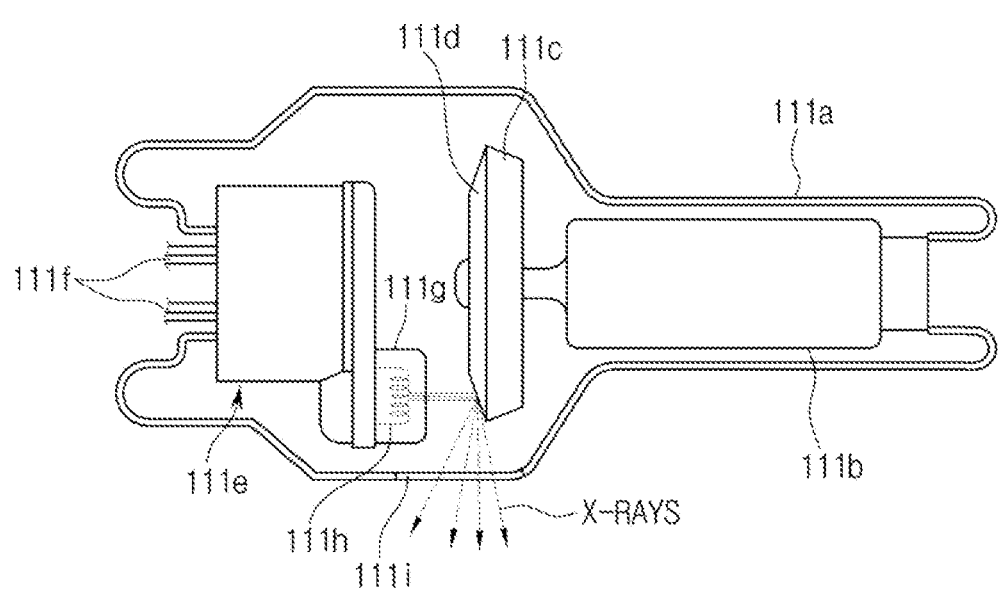
FIG. 3 is a diagram illustrating an exemplary configuration of an X-ray tube.

FIG. 3 is a diagram illustrating an exemplary configuration of an X-ray tube.

As illustrated in FIG. 3, the X-ray tube 111 may be implemented as a diode including an anode 111c and a cathode 111e. A tube body may be a glass tube 111a made of a silica hard glass or the like.

The cathode 111e includes a filament 111h and a focusing electrode 111g configured to focus electrons. The focusing electrode 111g is also referred to as a focusing cup. An inside of the glass tube 111a is maintained in a high vacuum state of about 10 mmHg, the filament 111h of the cathode is heated to a high temperature, and thermoelectrons are generated. As an example of the filament 111h, a tungsten filament may be used. The filament 111h may be heated by applying a current to an electrical conductor 111f connected to the filament. While FIG. 3 exemplarily illustrates the cathode 111e of the X-ray tube 111 using the filament 111h, this is only an example, and it is possible to use a carbon nano-tube capable of being driven in a high-speed pulse as the cathode.

The anode 111c is primarily made of copper, and a target material 111d is applied or disposed in a side facing the cathode 111e. A high-resistance material such as Cr, Fe, Co, Ni, W, or Mo may be used as the target material. As a melting point of the target material increases, a focal spot size decreases.

Also, when a high voltage is applied between the cathode 111e and the anode 111c, thermoelectrons are accelerated and collide with the target material 111d of the anode, and X-rays are generated. The generated X-rays are radiated to the outside through a window 111i, and a beryllium (Be) thin film may be used as a material of the window.

The target material 111d may be rotated by a rotor 111b. When the target material 111d rotates, a heat accumulation rate per unit area may increase tenfold or more than when the target material is fixed and the focal spot size decreases.

The voltage applied between the cathode 111e and the anode 111c of the X-ray tube 111 is referred to as a tube voltage, and a level thereof may be indicated as peak kilovoltage (kvp). As the tube voltage increases, speeds of thermoelectrons increase. As a result, energy (photon energy) of the X-rays generated by colliding with the target material increases. A current flowing in the X-ray tube 111 is referred to as a tube current and may be indicated as an average mA. As the tube current increases, a dose of X-rays (the number of X-rays photons) increases.

Therefore, the energy band of X-rays may be controlled by the tube voltage, and an intensity or a dose of X-rays may be controlled by the tube current and the X-ray exposure time. According to a type or a property of the object 35, the energy band and the intensity of radiated X-rays may be controlled.

The X-ray source 110 generates X-rays using the X-ray tube 111 described above, and radiates the generated X-rays onto the subject 30, and more specifically, onto the object 35.

When X-rays are radiated onto the object 35 from the X-ray source 110, an attenuation degree of X-rays varies depending on an internal material of the object 35 and the energy band of radiated X-rays. According to an exemplary embodiment, the attenuation degree of X-rays is numerally expressed as an attenuation coefficient.

The attenuation coefficient varies depending on the internal material of the object 35.

Figure 4:
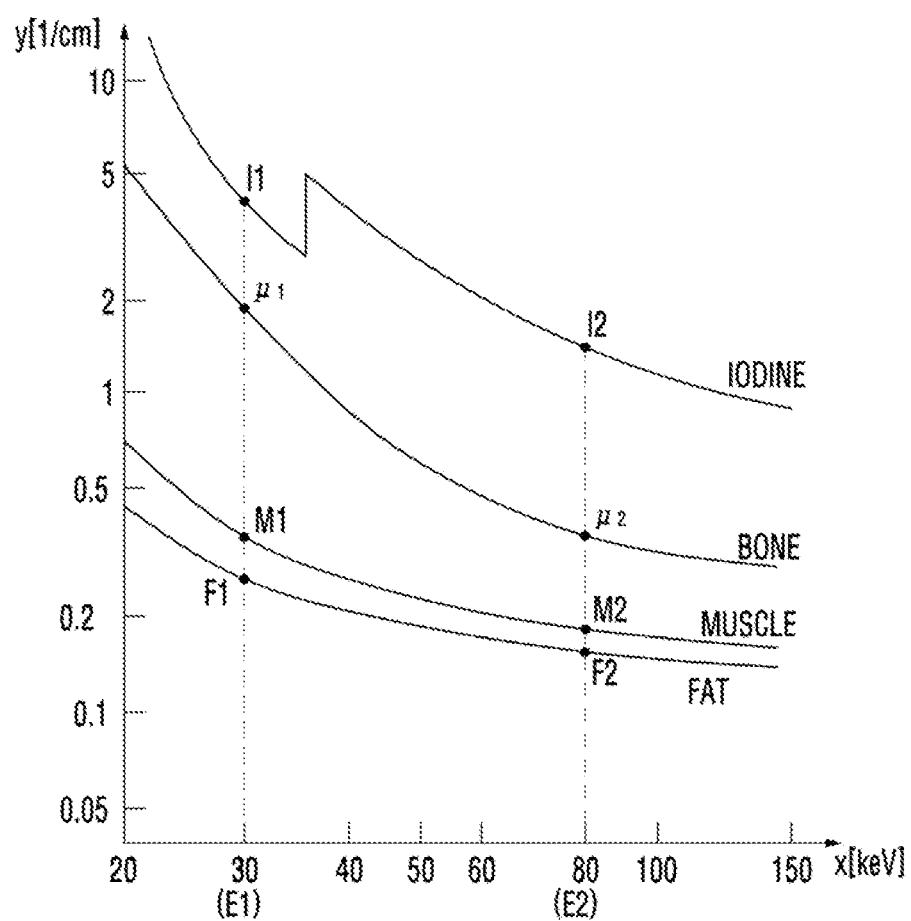
FIG. 4 is a graph showing a relation between energy and an attenuation coefficient for each material inside an object.

FIG. 4 describes an example of the attenuation coefficient varying depending on the internal material of the object 35. FIG. 4 is a graph showing a relation between energy and an attenuation coefficient for each material inside an object. An x axis represents a photon energy radiated onto the object 35. A y axis represents an attenuation coefficient.

As shown in the graph of FIG. 4, a curve representing an attenuation coefficient of a bone is positioned above a curve representing an attenuation coefficient of soft tissues (muscle and fat), and a curve representing an attenuation coefficient of iodine is positioned above the curve representing an attenuation coefficient of a bone. Specifically, when X-rays of the same energy band, for example, $E_1$, are radiated, an attenuation coefficient ($B_1$) of the bone is greater than an attenuation coefficient ($M_1$) of the muscle, the attenuation coefficient ($M_1$) of the muscle is greater than an attenuation coefficient ($F_1$) of the fat, and an attenuation coefficient ($I_1$) of the iodine is greater than the attenuation coefficient ($B_1$) of the bone.

That is, different materials inside the object 35 have different attenuation coefficients. As an atomic number or a density increases, the attenuation coefficient increases.

Further, the attenuation coefficient varies depending on the energy band of radiated X-rays.

As shown in the graph of FIG. 4, when X-rays of energy bands $E_1$ and $E_2$ are radiated onto the bone that is an internal material of the object 35, an attenuation coefficient ($B_1$) in the low energy band $E_1$ is greater than an attenuation coefficient ($B_2$) in the high energy band $E_2$. It can be understood that, when the internal material of the object 35 is muscle or fat, attenuation coefficients ($M_1$ and $F_1$) when the low energy band $E_1$ is radiated are greater than attenuation coefficients ($M_2$ and $F_2$) when the high energy band $E_2$ is radiated. In addition, a similar distribution may be observed in iodine.

That is, as the energy band of X-rays radiated onto the object 35 decreases, the attenuation coefficient increases.

The attenuation coefficient may be represented by the following [Equation 1]:

$$I = I_0 \cdot e^{-\mu(E) \cdot T} \qquad \text{[Equation 1]}$$

Here, $I_0$ represents an intensity of X-rays radiated onto an material, I represents an intensity of X-rays having penetrated through the material, and $\mu(E)$ represents an attenuation coefficient of the material for X-rays having an energy E. T represents a thickness of the material through which X-rays penetrate.

In Equation 1, it can be understood that, as the attenuation coefficient increases (that is, as the material becomes harder or the energy band of radiated X-rays decreases), and as the material becomes thicker, an intensity of penetrated X-rays decreases.

Referring again to FIG. 2, the X-ray detector 120 detects X-rays having penetrated through the object 35, converts the detected X-rays into an electrical signal, and obtains X-ray data.

In general, the X-ray detector 120 may be classified as various types according to a type of detection method used by the X-ray detector 120, including, for example, a material constituting method, a method of converting detected X-rays into an electrical signal, or a method of obtaining X-ray data. Hereinafter, various methods in which the X-ray detector detects X-rays, the detected X-rays are converted into an electrical signal, that is, raw data, and X-ray data is obtained will be described.

First, the X-ray detector 120 is classified according to a direct conversion method or an indirect conversion method according to a method of converting X-rays into raw data.

In the direct conversion method, when X-rays are radiated, electron-hole pairs are temporarily generated inside a light-receiving element, electrons move to the anode and holes move to the cathode due to an electric field applied to both ends of the light-receiving element, and the X-ray detector 120 converts such movement into an electrical signal. In the direct conversion method, a material used in the light-receiving element includes a-Se, CdZnTe, $HgI_2$, $PbI_2$, or the like.

In the indirect conversion method, a scintillator is provided between the light-receiving element and the X-ray source 110. When X-rays radiated from the X-ray source 110 react with the scintillator and emit photons having a wavelength of a visible light region, the light-receiving element detects the photons and converts the photons into an electrical signal. In the indirect conversion method, a material used in the light-receiving element includes a-Si or the like. As the scintillator, a thin-film GADOX scintillator, a micro columnar or needle-shaped CSI (T1), or the like is used.

In addition, according to a method of obtaining raw data, the X-ray detector 120 is classified into one of a charge integration mode in which electric charges are stored for a predetermined time and then a signal is obtained therefrom or a photon counting mode in which photons having a threshold energy or higher are counted whenever a signal is generated by a single X-ray photon.

The X-ray detector 120 may obtain a plurality of pieces of raw data of different energy bands. Specifically, when the X-ray source radiates multi-energy X-rays, the X-ray detector 120 classifies detected X-rays for each energy band, and a plurality of pieces of raw data may be obtained.

For example, when the X-ray detector 120 uses the photon counting mode, the X-ray detector 120 may be designed to have a plurality of threshold energies. As a result, the X-ray detector 120 may obtain a plurality of pieces of raw data that are classified by each of the plurality of threshold energies.

On the other hand, the X-ray source radiates single-energy X-rays of different energy bands multiple times, the X-ray detector 120 detects X-rays having penetrated through the object multiple times, and a plurality of pieces of raw data of different energy bands may be obtained.

Referring again to FIG. 2, the material image separating unit 210 may generate at least one material image using the plurality of pieces of raw data of different energy bands.

A material image separated by the material separating unit 210 is not limited to any particular type and the material image can be separated as long as the material has a different X-ray attenuation coefficient. For example, a material to be separated may include a bone and a soft tissue, a lesion tissue and a non-lesion tissue, and a calcified tissue and a non-calcified tissue. The calcified tissue may include a calcified nodule and the non-calcified tissue may include a non-calcified nodule.

In addition, when the object is a breast, at least one material selected from the group including an adipose tissue, a parenchymal tissue, a calcified tissue, and a lesion tissue may be separated.

The material image separating unit 210 may convert the plurality of pieces of raw data of different energy bands into a plurality of original images of different energy bands. In this case, the original image may have the form of a raw image.

The material image separating unit 210 may separate a plurality of material images by performing two computations including multiplying at least one of the plurality of original images by a weight and then performing subtraction. This technique is also referred to as multi-energy X-ray absorptiometry.

For example, when a material to be separated is a bone and a soft tissue, a soft tissue image may be obtained when an original image (hereinafter referred to as a "low energy image") corresponding to a low energy band is multiplied by a predetermined weight and then is subtracted from an original image (hereinafter referred to as a "high energy image") corresponding to a high energy band. That is, it is possible to obtain an image in which the bone is removed and the soft tissue is clearly visible.

On the other hand, a bone image may be obtained when the high energy image is multiplied by a predetermined weight and then is subtracted from the low energy image. That is, it is possible to obtain an image in which the soft tissue is removed and the bone is clearly visible.

Also, the soft tissue image or the bone image may be obtained when the low energy image and the high energy image are multiplied by an appropriate weight and then subtraction is performed.

In addition, when a material to be separated is a lesion tissue and a non-lesion tissue, or a calcified tissue and a non-calcified tissue, the above method may be used. However, according to an area of the object, the lesion tissue may be included in the calcified tissue or the non-calcified tissue.

As another example, when the object is the breast composed of the soft tissue and a material to be separated is a glandular tissue (which may also referred to as a "parenchymal tissue") and an adipose tissue, the low energy image and the high energy image are multiplied by an appropriate weight and then subtraction is performed. Therefore, a glandular tissue image and an adipose tissue image may be separated.

As still another example, when there are three or more types of materials to be separated, the material separating unit 210 may obtain three or more original images corresponding to three or more energy bands, respectively, multiply each of the images by an appropriate weight, perform subtraction, and separate three or more types of material images. Specifically, when the object is the breast, three or more types of material images selected from the group including an adipose tissue, a parenchymal tissue, a calcified tissue, and a lesion tissue may be separated.

As described above, a type of the material to be separated or the number thereof is not limited, and the material image separating unit 210 may obtain an original image according to the number of materials to be separated and separate each material image using an attenuation property for each material.

Figure 5:
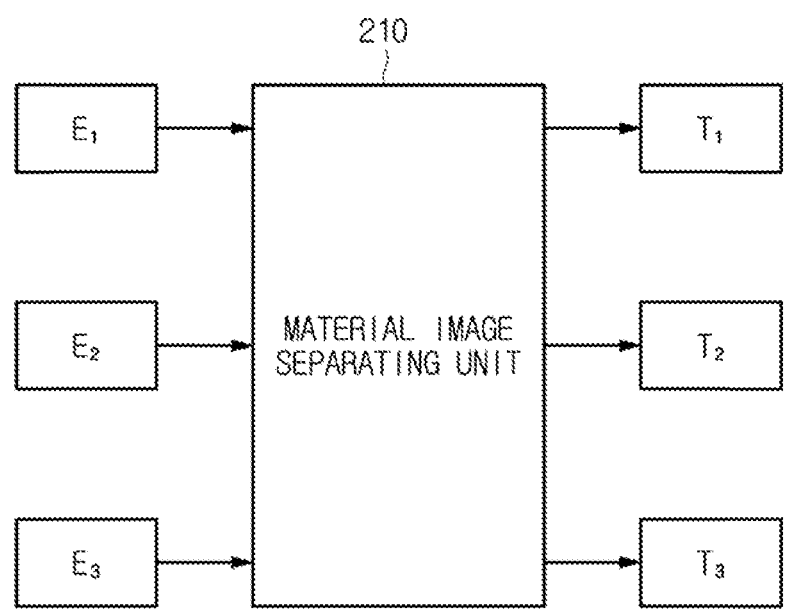
FIG. 5 is a diagram illustrating an operation of a material separating unit of an X-ray apparatus according to an exemplary embodiment.

FIG. 5 is a diagram illustrating an operation of the material image separating unit 210 of an X-ray apparatus according to an exemplary embodiment.

In FIG. 5, $E_1$ may denote X-ray data of a first energy band, $E_2$ may denote X-ray data of a second energy band, and $E_3$ may denote X-ray data of a third energy band. In addition, $T_1$ may denote a first material image in which a first material is separated, $T_2$ may denote a second material image in which a second material is separated, and $T_3$ may denote a third material image in which a third material is separated.

As illustrated in FIG. 5, the material separating unit 210 may receive the X-ray data of the first energy band, the X-ray data of the second energy band, and the X-ray data of the third energy band obtained by the X-ray detector 120.

Next, the material image separating unit 210 may convert the received X-ray data into an original image. Specifically, the material image separating unit 210 may convert the X-ray data of the first energy band into an original image of the first energy band, convert the X-ray data of the second energy band into an original image of the second energy band, and convert the X-ray data of the third energy band into an original image of the third energy band.

After the original images of different energy bands are obtained, the material image separating unit 210 may generate at least one material image in which at least one material is separated from the original image. Specifically, the material image separating unit 210 may generate a first material image in which the first material is separated by applying a weight to at least one of the original image of the first energy band, the original image of the second energy band, and the original image of the third energy band and performing subtraction. In addition, the material image separating unit 210 may generate a second material image in which the second material is separated by applying a weight to at least one of the original image of the first energy band, the original image of the second energy band, and the original image of the third energy band and performing subtraction. According to the same method, the material image separating unit 210 may generate a third material image.

The X-ray apparatus may provide the material image generated by the material image separating unit 210 to the user and provide an image in which the X-ray image of the object and the material image are synthesized to the user. Accordingly, the X-ray apparatus may provide an image in which the separated material is enhanced inside the object.

In this case, the X-ray apparatus may generate the X-ray image of the object using the plurality of pieces of raw data obtained by the X-ray detector 120. According to an exemplary embodiment, the X-ray image of the object may refer to an image including information on an anatomical structure of the object.

Hereinafter, based on operations of the raw image obtaining unit 220, the image processing unit 230, and the synthesizing unit 240, a method of generating an X-ray image of an object and synthesizing the X-ray image and a material image will be described in detail.

Referring again to FIG. 2, the raw image obtaining unit 220 may obtain a plurality of raw images in which different materials constituting the object are enhanced using a plurality of pieces of X-ray data of different energy bands. According to an exemplary embodiment, the raw image may refer to an image before image processing is performed.

Specifically, the raw image obtaining unit 220 may apply a weight corresponding to a specific material to each of the plurality of pieces of raw data detected by the X-ray detector 120. Then, the raw image obtaining unit 220 may obtain a raw image in which a specific material is enhanced by summing the plurality of pieces of raw data to which the weight is applied.

When the above method is repeated by changing the weight according to a specific material to be enhanced, the raw image obtaining unit 220 may obtain a plurality of raw images in which different materials are enhanced.

Figure 6:
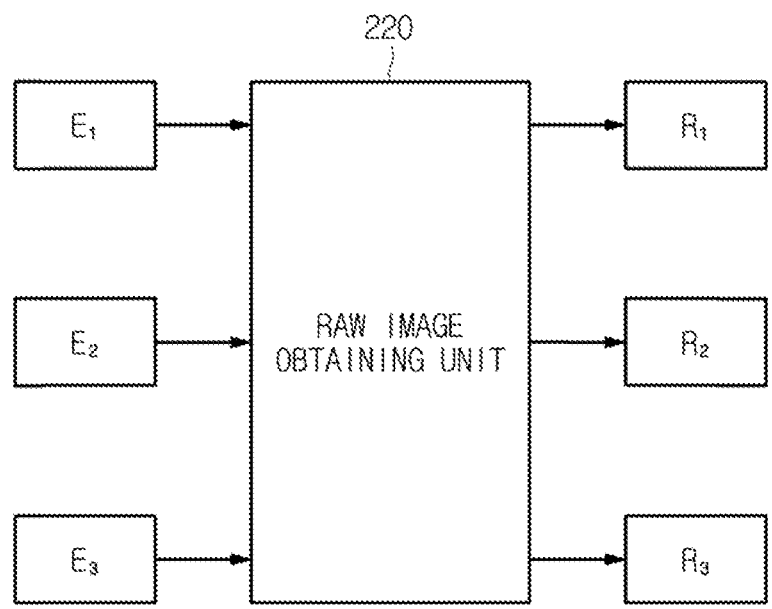
FIG. 6 is a diagram illustrating an operation of a raw image obtaining unit of an X-ray apparatus according to an exemplary embodiment.
Figure 7:
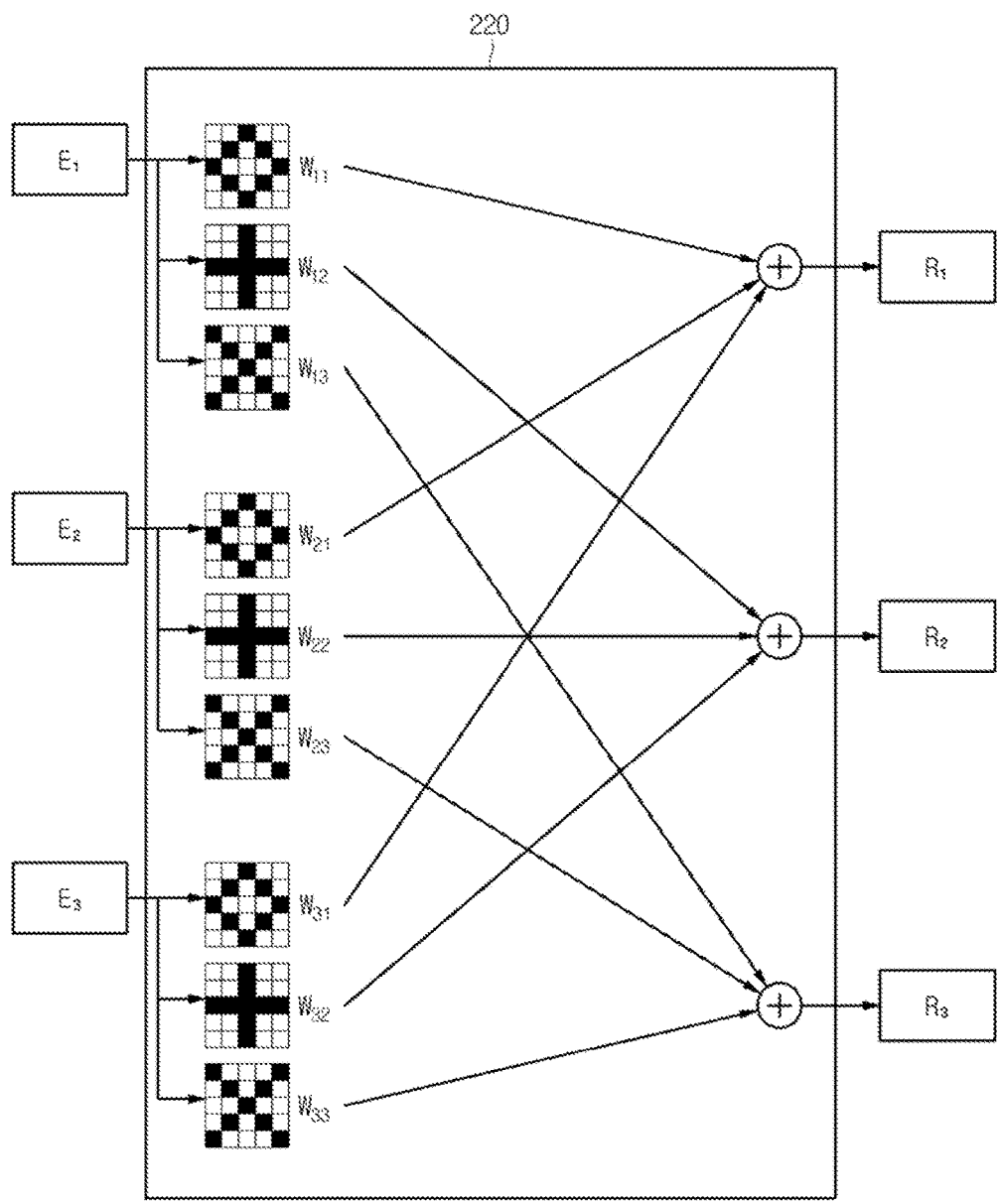
FIG. 7 is a diagram illustrating the operation of the raw image obtaining unit in detail.

FIG. 6 is a diagram illustrating an operation of a raw image obtaining unit of an X-ray apparatus according to an exemplary embodiment. FIG. 7 is a diagram illustrating the operation of the raw image obtaining unit in detail.

In FIGS. 6 and 7, $E_1$ may denote X-ray data of a first energy band, $E_2$ may denote X-ray data of a second energy band, and $E_3$ may denote X-ray data of a third energy band. In addition, $R_1$ may denote a first raw image in which a first material is enhanced, $R_2$ may denote a second raw image in which a second material is enhanced, and $R_3$ may denote a third raw image in which a third material is enhanced.

As illustrated in FIG. 6, the raw image obtaining unit 220 may receive the X-ray data of the first energy band, the X-ray data of the second energy band, and the X-ray data of the third energy band obtained by the X-ray detector 120.

Then, the raw image obtaining unit 220 may apply a weight corresponding to the first material to each of the plurality of pieces of raw data. In this case, the weight applied to each of the plurality of pieces of raw data may be different.

Finally, the raw image obtaining unit 220 may obtain a first raw image in which the first material is enhanced by summing each of the plurality of pieces of raw data to which the weight is applied. In this case, the raw image obtaining unit 220 may obtain the first raw image by summing data corresponding to the same pixel in each of the plurality of pieces of raw data.

For example, the raw image obtaining unit 220 may sum data determining a pixel value of (1,1) of the first raw image among first raw data, data determining a pixel value of (1,1) of the first raw image among second raw data, and data determining a pixel value of (1,1) of the first raw image among third raw data.

In addition, the raw image obtaining unit 220 may obtain a second raw image by applying a weight corresponding to the second material that is different from the first material to each of the plurality of pieces of raw data and summing the plurality of pieces of raw data to which the weight is applied. In this case, the weight applied to each of the plurality of pieces of raw data may be different.

According to the same method, the raw image obtaining unit 220 may obtain a third raw image.

Specifically, as illustrated in FIG. 7, the raw image obtaining unit 220 may apply a weight $W_{11}$ corresponding to the first material to the first raw data. According to an exemplary embodiment, the weight corresponding to the first material may refer to a weight that is applied to data corresponding to a pixel in which the first material is displayed in the raw image. FIG. 7 exemplifies that pixels (black) in which the first material is displayed in the raw image form a diamond shape.

In addition, the raw image obtaining unit 220 may apply a weight $W_{21}$ corresponding to the first material to the second raw data. Similarly, the raw image obtaining unit 220 may apply a weight $W_{31}$ corresponding to the first material to the third raw data.

In this manner, the raw image obtaining unit 220 may apply different weights $W_{11}$, $W_{21}$, and $W_{31}$ corresponding to the first material to each of the plurality of pieces of raw data.

Then, the raw image obtaining unit 220 may obtain a first raw image $R_1$ in which the first material is enhanced by summing the plurality of pieces of raw data at the first, second and third energy bands $E_1$, $E_2$, and $E_3$ to which different weights $W_{11}$, $W_{21}$, and $W_{31}$ are applied.

At the same time as obtaining the first raw image R1 or sequentially after obtaining the first raw image R1, the raw image obtaining unit 220 may apply a weight $W_{12}$ corresponding to the second material to the first raw data. Here, the weight corresponding to the second material may refer to a weight applied to data corresponding to a pixel in which the second material is displayed in the raw image. FIG. 7 exemplifies that pixels (black) in which the second material is displayed in the raw image form a cross shape.

In addition, the raw image obtaining unit 220 may apply a weight $W_{22}$ corresponding to the second material to the second raw data. Similarly, the raw image obtaining unit 220 may apply a weight $W_{32}$ corresponding to the second material to the third raw data.

Then, the raw image obtaining unit 220 may obtain a second raw image R2 in which the second material is enhanced by summing the plurality of pieces of raw data at the first, second and third energy bands $E_1$, $E_2$ and $E_3$ to which different weight $W_{12}$, $W_{22}$, and $W_{32}$ are applied.

According to the same method, the raw image obtaining unit 220 may obtain a third raw image in which the third material is enhanced by applying weights $W_{13}$, $W_{23}$, and $W_{33}$ corresponding to the third material to each of the plurality of pieces of raw data at the first, second and third energy bands $E_1$, $E_2$, and $E_3$ and summing the results.

Referring again to FIG. 2, the image processing unit 230 may generate the X-ray image of the object by processing a plurality of raw images in which each of the plurality of materials is enhanced. Specifically, the image processing unit 230 may process each of the plurality of raw images based on a parameter value determined by the enhanced material.

Figure 8:
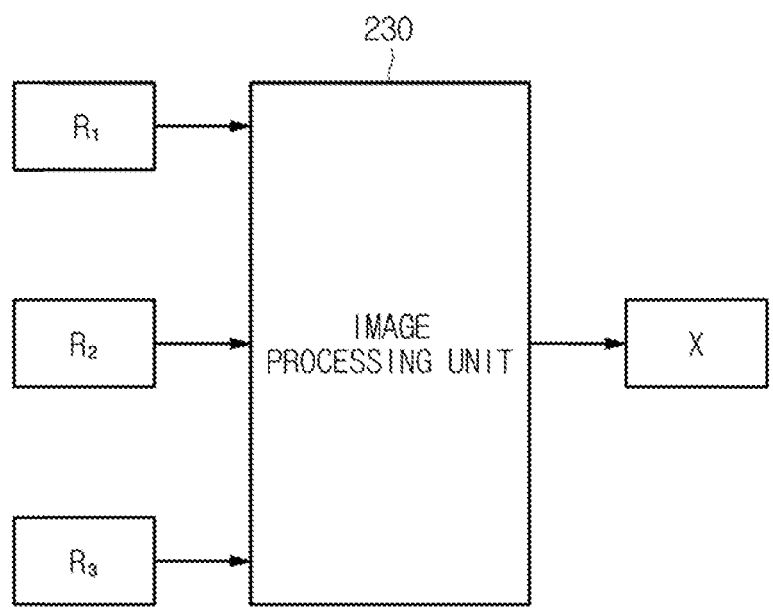
FIG. 8 is a diagram illustrating an operation of an image processing unit of an X-ray apparatus according to an exemplary embodiment.
Figure 9:
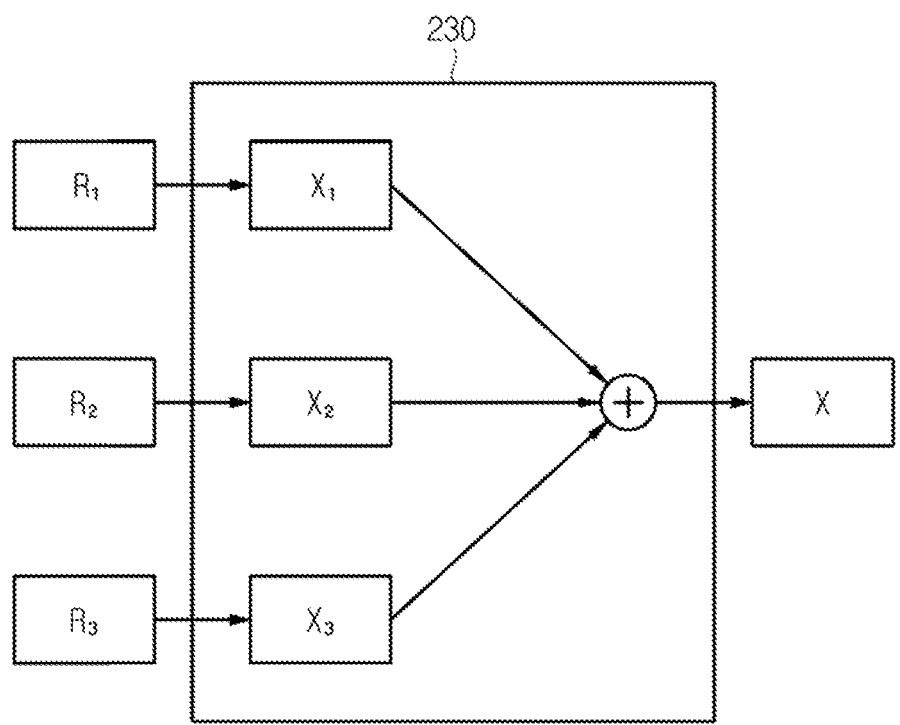
FIG. 9 is a diagram illustrating the operation of the image processing unit in detail.

FIG. 8 is a diagram illustrating an operation of an image processing unit of an X-ray apparatus according to an exemplary embodiment. FIG. 9 is a diagram illustrating the operation of the image processing unit in detail.

In FIGS. 8 and 9, $R_1$ may denote a first raw image in which the first material is enhanced, $R_2$ may denote a second raw image in which the second material is enhanced, and $R_3$ may denote a third raw image in which the third material is enhanced. In addition, $X_1$ may denote a first X-ray image that is generated by processing the first raw image, $X_2$ may denote a second X-ray image that is generated by processing the second raw image, and $X_3$ may denote a third X-ray image that is generated by processing the third raw image. In addition, X may denote the X-ray image of the object that is finally generated by the image processing unit 230.

As illustrated in FIG. 8, the image processing unit 230 may receive the first raw image, the second raw image, and the third raw image obtained by the raw image obtaining unit 220.

Then, the image processing unit 230 may process each of the plurality of raw images according to a predetermined image processing algorithm, sum the results, and generate the X-ray image of the object.

According to an exemplary embodiment, as the predetermined image processing algorithm, any of known algorithms that are used to process a raw image to an X-ray image provided for the user may be selected and applied.

In this case, a parameter value used in the image processing algorithm may be determined according to a material that is enhanced in each raw image. The parameter value may be determined by a software or hardware configuration inside the X-ray apparatus or determined by the user's input.

The parameter used in the image processing algorithm may include a parameter for image enhancement. The parameter used in the image processing algorithm may include at least one of contrast enhancement (CE), edge enhancement (EE), a frequency, latitude compression (LC), and a look up table (LUT).

The CE is a parameter for representing contrast enhancement of an image due to a concentration difference based on a light exposure amount. When a CE value is increased, an image of areas of being observed (e.g., intestines in the abdomen, mediastinum in the chest, etc.) may be enhanced.

The EE is a parameter for representing an edge enhancement change in image pixel margins by distinguishing a boundary of tissues. When an EE value is increased, an image of small blood vessels in the chest and calcification may be partially enhanced.

The frequency may represent a frequency change of an image in the image. A frequency value may be used in a filtering process of the image.

The LC is used when an image is not uniform due to contrast and is a parameter for representing a dynamic range. When an LC value is increased, areas being observed (e.g., a lung tissue in the chest, a translucent area of pelvis and thoracic vertebra in the abdomen, a cranial bone and a soft tissue, etc.) may be enhanced.

The LUT may represent a table in which a predetermined parameter value is set when the X-ray apparatus is manufactured. When a level of the LUT is determined, a parameter value corresponding to the level may be determined. The parameter value corresponding to the level may form any of a linear, sigmoid, logarithmic, exponential, and gamma curve.

When the parameter value is changed in this manner, a desired material may be enhanced. Therefore, when a raw image in which a specific material is enhanced is processed using a parameter value that is determined to enhance the specific material, it is possible to obtain an X-ray image having further improved image quality.

Specifically, as illustrated in FIG. 9, the image processing unit 230 may generate a first X-ray image by processing a first raw image in which the first material is enhanced according to a predetermined image processing algorithm. In this case, a parameter value used in the image processing algorithm may be determined to correspond to the first material.

Similarly, the image processing unit 230 may generate a second X-ray image by processing a second raw image in which the second material is enhanced according to a predetermined image processing algorithm. In this case, a parameter value used in the image processing algorithm may be determined to correspond to the second material.

Similarly, the image processing unit 230 may generate a third X-ray image by processing a third raw image in which the third material is enhanced according to a predetermined image processing algorithm. In this case, a parameter value used in the image processing algorithm may be determined to correspond to the third material.

Finally, the image processing unit 230 may generate the X-ray image of the object by summing the first X-ray image, the second X-ray image, and the third X-ray image. The X-ray image generated in this manner may include information on an anatomical structure of the object.

According to the above-described method, the generated X-ray image may have an improved contrast-to-noise ratio (CNR) compared to an X-ray image that is obtained by radiating X-rays of a single energy band. This improved CNR is because a parameter value corresponding to each configuration is determined to perform image processing and the results are summed to generate the X-ray image of the object.

Referring again to FIG. 2, the synthesizing unit 240 may synthesize the X-ray image generated by the image processing unit 230 and the material image generated by the material separating unit 210. As a result, finally, the synthesizing unit 240 may generate a final image.

Figure 10:
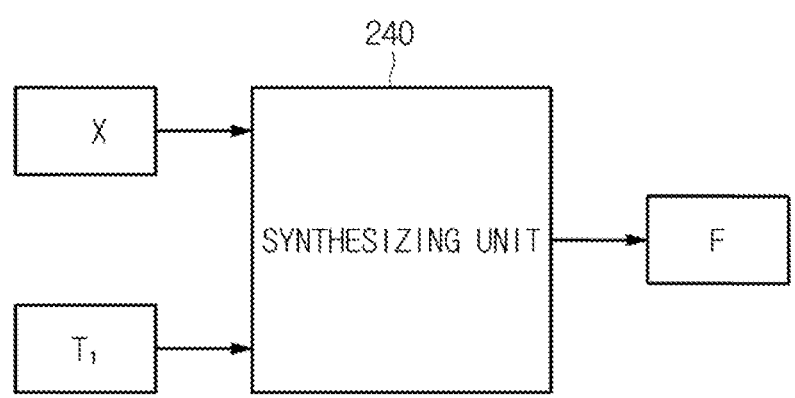
FIG. 10 is a diagram illustrating an operation of a synthesizing unit of an X-ray apparatus according to an exemplary embodiment.

FIG. 10 is a diagram illustrating an operation of a synthesizing unit of an X-ray apparatus according to an exemplary embodiment.

In FIG. 10, X may denote the X-ray image of the object in the image processing unit 230 and $T_1$ may denote the first material image in which the first material is separated. In addition, F may denote the final image in which the X-ray image of the object and the material image are synthesized.

The synthesizing unit 240 may receive the X-ray image from the image processing unit 230 and receive at least one material image from the material separating unit 210. FIG. 10 exemplifies a case in which the synthesizing unit 240 receives the X-ray image X and the first material image $T_1$.

The synthesizing unit 240 may synthesize the received images and generate the final image to be displayed on the display 172. Specifically, the X-ray image in which the anatomical structure of the object is displayed and the first material image in which the first material constituting the object is displayed may be synthesized to generate the final image F. In this case, the synthesizing unit 240 may register and synthesize the X-ray image and the first material image.

As a result, the synthesizing unit 240 may generate the final image in which the anatomical structure of the object and a shape of the first material inside the object are enhanced.

The final image generated in this manner may be displayed through the display 172 and be provided to the user.

FIG. 11 is a flowchart schematically illustrating a method of generating an X-ray image according to an exemplary embodiment.

First, X-rays are radiated onto the object in operation 300. In this case, multi-energy X-rays may be radiated at least once, or X-rays of different energy bands may be radiated multiple times.

Next, the plurality of pieces of raw data of different energy bands are obtained in operation 310. When multi-energy X-rays are radiated at least once, raw data may be obtained by classifying each of the energy bands. On the other hand, when X-rays of different energy bands are radiated multiple times, raw data may be obtained which corresponds to the radiated X-rays.

When the plurality of pieces of raw data obtained in this manner are used, it is possible to obtain a plurality of raw images in which different materials constituting the object are enhanced in operation 320.

For this purpose, a weight corresponding to a material to be enhanced may be applied to the plurality of pieces of raw data. Then, the plurality of pieces of raw data to which the weight is applied may be summed to obtain a raw image in which the corresponding material is enhanced.

Finally, the plurality of raw images are processed to generate the X-ray image of the object in operation 330. In this case, the generated X-ray image of the object may include information on the anatomical structure of the object.

In particular, a parameter value used in the image processing algorithm may be determined to correspond to the material enhanced in the raw image. As a result, the finally generated X-ray image may be an image having an improved CNR.

FIG. 12 is a detailed flowchart illustrating a method of generating an X-ray image according to an exemplary embodiment.

First, X-rays are radiated onto the object in operation 400. Specifically, multi-energy X-rays including the first energy band, the second energy band, and the third energy band may be radiated once or X-rays of the first energy band, X-rays of the second energy band, and X-rays of the third energy band may be sequentially radiated.

Next, a plurality of pieces of raw data $E_1$, $E_2$, and $E_3$ of different energy bands are obtained in operation 410.

When multi-energy X-rays are radiated, first raw data $E_1$ may be obtained using X-rays of the first energy band among detected X-rays, second raw data $E_2$ may be obtained using X-rays of the second energy band among detected X-rays, and third raw data $E_3$ may be obtained using X-rays of the third energy band among detected X-rays.

On the other hand, when X-rays of the first energy band, X-rays of the second energy band, and X-rays of the third energy band are sequentially radiated, first raw data $E_1$ may be obtained when X-rays of the first energy band are radiated, second raw data $E_2$ may be obtained when X-rays of the second energy band are radiated, and third raw data $E_3$ may be obtained when X-rays of the third energy band are radiated.

Then, weights $W_{11}$, $W_{12}$, $W_{13}$ for enhancing materials $M_1$, $M_2$, and $M_3$ are applied to the first raw data E1 in operation 420a. As a result, $E_1$ to which the weight $W_{11}$ is applied, $E_1$ to which the weight $W_{12}$ is applied, and $E_1$ to which the weight $W_{13}$ is applied are obtained.

Similarly, weights $W_{21}$, $W_{22}$, and $W_{23}$ for enhancing materials $M_1$, $M_2$, and $M_3$ are applied to the second raw data $E_2$ in operation 420b. As a result, $E_2$ to which the weight $W_{21}$ is applied, $E_2$ to which the weight $W_{22}$ is applied, and $E_2$ to which the weight $W_{23}$ is applied are obtained.

Similarly, weights $W_{31}$, $W_{32}$, and $W_{33}$ for enhancing materials $M_1$, $M_2$, and $M_3$ are applied to the third raw data $E_3$ in operation 420c. As a result, $E_3$ to which the weight $W_{31}$ is applied, $E_3$ to which the weight $W_{32}$ is applied, and $E_3$ to which the weight $W_{33}$ is applied are obtained.

Next, $E_1$ to which the weight $W_{11}$ is applied, $E_2$ to which the weight $W_{21}$ is applied, and $E_3$ to which the weight $W_{31}$ is applied are summed to obtain a raw image $R_1$ in which the material $M_1$ is enhanced in operation 430a. Since $W_{11}$, $W_{21}$, and $W_{31}$ are weights that are applied to each of the plurality of pieces of raw data in order to enhance the material $M_1$, the material $M_1$ is enhanced in the raw image $R_1$ that is generated after the weight is applied and data is summed.

Similarly, $E_1$ to which the weight $W_{12}$ is applied, $E_2$ to which the weight $W_{22}$ is applied, and $E_3$ to which the weight $W_{32}$ is applied are summed to obtain a raw image $R_2$ in which the material $M_2$ is enhanced in operation 430b. Since $W_{12}$, $W_{22}$, and $W_{32}$ are weights that are applied to each of the plurality of pieces of raw data in order to enhance the material $M_2$, the material $M_2$ is enhanced in the raw image $R_2$ that is generated after the weight is applied and data is summed.

In addition, $E_1$ to which the weight $W_{13}$ is applied, $E_2$ to which the weight $W_{23}$ is applied, and $E_3$ to which the weight $W_{33}$ is applied are summed to obtain a raw image $R_3$ in which the material $M_3$ is enhanced in operation 430c. Since $W_{13}$, $W_{23}$, and $W_{33}$ are weights that are applied to each of the plurality of pieces of raw data in order to enhance the material $M_3$, the material $M_3$ is enhanced in the raw image $R_3$ that is generated after the weight is applied and data is summed.

Next, the raw image $R_1$ is processed using a parameter value corresponding to the material $M_1$ in operation 440a. According to an exemplary embodiment, the parameter value corresponding to the material $M_1$ may refer to a parameter value used for enhancing the material $M_1$ when image processing is performed using the image processing algorithm.

According to an exemplary embodiment, the parameter may include at least one of contrast enhancement (CE), edge enhancement (EE), a frequency, latitude compression (LC), and a look up table (LUT).

Similarly, the raw image $R_2$ is processed using a parameter value corresponding to the material $M_2$ in operation 440b. According to an exemplary embodiment, the parameter value corresponding to the material $M_2$ may refer to a parameter value used for enhancing the material $M_2$ when image processing is performed using the image processing algorithm.

In addition, the raw image $R_3$ is processed using a parameter value corresponding to the material $M_3$ in operation 440c. According to an exemplary embodiment, the parameter value corresponding to the material $M_3$ may refer to a parameter value used for enhancing the material $M_3$ when image processing is performed using the image processing algorithm.

Finally, the image-processed $R_1$, $R_2$, and $R_3$ are summed to generate the X-ray image X in operation 450. The X-ray image generated in this manner may be an image in which $M_1$, $M_2$, and $M_3$ are enhanced and may have an improved CNR compared to an image that is obtained by X-rays of a single energy band.

According to an aspect of the X-ray apparatus and the method of controlling the same according to exemplary embodiments, an X-ray image having improved image quality for each material may be obtained by applying a material-adaptive weight to X-ray data of a plurality of different energy bands.

According to another aspect of the X-ray apparatus and the method of controlling the same according to exemplary embodiments, an image in which an anatomical structure of an object can be clearly recognized may be provided by synthesizing an X-ray image having improved image quality for each material and the material image.

Although a few exemplary embodiments have been shown and described, it would be appreciated by those skilled in the art that changes may be made in these exemplary embodiments without departing from the principles and spirit of the exemplary embodiments, the scope of which is defined in the claims and their equivalents.

What is claimed is:

1. An X-ray apparatus, comprising:
    an X-ray source configured to radiate X-rays onto an object;
    an X-ray detector configured to detect X-rays having penetrated through the object among the radiated X-rays and obtain pieces of raw data of different energy bands based on the detected X-rays, the pieces of raw data comprising a first piece of raw data corresponding to a first energy band among the different energy bands and a second piece of raw data corresponding to a second energy band among the different energy bands; and
    at least one processor configured to:
    apply a first weight, that corresponds to a first material, to the first piece of raw data and the second piece of raw data;
    obtain a first raw image in which the first material is enhanced based on applying the first weight that corresponds to the first material, to the first piece of raw data and the second piece of raw data;
    apply a second weight, that corresponds to a second material, to the first piece of raw data and the second piece of raw data;
    obtain a second raw image in which the second material is enhanced based on applying the second weight, that corresponds to the second material, to the first piece of raw data and the second piece of raw data; and
    process the first raw image and the second raw image and generate an X-ray image of the object by summing an image-processed first raw image and an image-processed second raw image,
    wherein the at least one processor is further configured to generate the X-ray image in which the first material and the second material are enhanced.

2. The X-ray apparatus according to claim 1,
    wherein the at least one processor is further configured to synthesize a material image separated from an image of the object with the X-ray image.

3. The X-ray apparatus according to claim 1,
    wherein the at least one processor is further configured to sum the first piece of raw data and the second piece of raw data to which the first weight is applied to thereby generate first summed pieces of raw data, and obtain the first raw image in which the first material is enhanced based on the first summed pieces of raw data.

4. The X-ray apparatus according to claim 1,
    wherein the at least one processor is further configured to process the first raw image and the second raw image based on a parameter value that is determined according to one of the enhanced materials.

5. The X-ray apparatus according to claim 1,
    wherein the X-ray source is configured to radiate multi-energy X-rays at least once or radiate X-rays of different energy bands multiple times.

6. The X-ray apparatus according to claim 2,
    wherein the at least one processor is further configured to register the material image and the X-ray image.

7. The X-ray apparatus according to claim 2,
    wherein the at least one processor is further configured to generate the material image using the pieces of raw data of different energy bands.

8. The X-ray apparatus according to claim 3,
    wherein the at least one processor is further configured to sum the first piece of raw data and the second piece of raw data to which the second weight is applied to thereby generate second summed pieces of raw data, and obtain the second raw image in which the second material is enhanced based on the second summed pieces of raw data.

9. The X-ray apparatus according to claim 3,
    wherein the at least one processor is further configured to apply different weights corresponding to the first material to the pieces of raw data of different energy bands to thereby obtain the first raw image.

10. The X-ray apparatus according to claim 3,
    wherein the at least one processor is further configured to sum data corresponding to a same pixel in the pieces of raw data to thereby obtain the first raw image in which the first material is enhanced.

11. The X-ray apparatus according to claim 4,
    wherein the parameter value corresponds to a parameter comprising at least one of contrast enhancement (CE), edge enhancement (EE), a frequency, latitude compression (LC), and a look up table (LUT).

12. A method of controlling an X-ray apparatus, comprising:
    radiating X-rays onto an object;
    detecting X-rays having penetrated through the object among the radiated X-rays and obtaining pieces of raw data of different energy bands based on the detected X-rays, the pieces of raw data comprising a first piece of raw data corresponding to a first energy band among the different energy bands and a second piece of raw data corresponding to a second energy band among the different energy bands;
    applying a first weight, that corresponds to a first material, to the first piece of raw data and the second piece of raw data;
    obtaining a first raw image in which the first material is enhanced based on applying the first weight, that corresponds to the first material, to the first piece of raw data and the second piece of raw data;
    applying a second weight, that corresponds to a second material, to the first piece of raw data and the second piece of raw data;
    obtaining a second raw image in which the second material is enhanced based on applying the second weight, that corresponds to the second material, to the first piece of raw data and the second piece of raw data; and
    processing the first raw image and the second raw image and generating an X-ray image of the object by summing an image-processed first raw image and an image-processed second raw image,
    wherein generating the X-ray image of the object comprises generating the X-ray image in which the first material and the second material are enhanced.

13. The method according to claim 12, further comprising synthesizing a material image separated from an image of the object with the X-ray image.

14. The method according to claim 12, further comprising:

summing the first piece of raw data and the second piece of raw data to which the first weight is applied; and wherein obtaining the first raw image comprises:

obtaining the first raw image based on summing the first piece of raw data and the second piece of raw data.

15. The method according to claim 12, wherein the processing the raw images comprises:

processing the first raw image based on a parameter value determined according to the first material.

16. The method according to claim 12, wherein the radiating of the X-rays comprises radiating multi-energy X-rays at least once or X-rays of different energy bands multiple times.

17. The method according to claim 13, wherein the synthesizing comprises registering the material image and the X-ray image.

18. The method according to claim 13, further comprising generating the material image using the pieces of raw data of different energy bands.

19. The method according to claim 14, further comprising:

summing the first piece of raw data and the second piece of raw data to which the second weight is applied; and wherein obtaining the second raw image comprises:

obtaining the second raw image based on summing the first piece of raw data and the second piece of raw data.

20. The method according to claim 14, further comprising:

applying different weights corresponding to the first material to the pieces of raw data of different energy bands for the different energy bands; and wherein the obtaining the first raw image comprises:

obtaining the first raw image based on applying the different weights corresponding to the first material to the pieces of raw data of different energy bands for the different energy bands.

21. The method according to claim 14, further comprising:

summing data corresponding to a same pixel in the pieces of raw data; and obtaining the first raw image in which the first material is enhanced based on summing the data corresponding to the same pixel in the pieces of raw data.

22. The method according to claim 15, wherein the parameter value corresponds to a parameter comprising at least one of contrast enhancement (CE), edge enhancement (EE), a frequency, latitude compression (LC), and a look up table (LUT).

* * * * *